US009029819B2

(12) United States Patent
Zhu et al.

(10) Patent No.: US 9,029,819 B2
(45) Date of Patent: May 12, 2015

(54) GAS DETECTION SYSTEM USING INTRACAVITY FIBER LASER WITH LOOP CAVITY HAVING SATURATED ABSORPTION FIBER

(71) Applicant: Beijing Information Science & Technology University, Beijing (CN)

(72) Inventors: Lianqing Zhu, Beijing (CN); Fei Luo, Winchester, MA (US); Mingli Dong, Beijing (CN); Wei He, Beijing (CN); Yinmin Zhang, Beijing (CN); Xiaochen Meng, Beijing (CN); Zhehai Zhou, Beijing (CN)

(73) Assignee: Beijing Information Science & Technology University, Beijing (CN)

( * ) Notice: Subject to any disclaimer, the term of this patent is extended or adjusted under 35 U.S.C. 154(b) by 0 days.

(21) Appl. No.: 14/509,604

(22) Filed: Oct. 8, 2014

(65) Prior Publication Data

US 2015/0102240 A1 Apr. 16, 2015

(30) Foreign Application Priority Data

Oct. 14, 2013 (CN) .......................... 2013 1 0479313

(51) Int. Cl.
*G01N 21/17* (2006.01)
*G01J 3/42* (2006.01)
(Continued)

(52) U.S. Cl.
CPC ............ *G01N 21/61* (2013.01); *G01N 33/0027* (2013.01); *G01J 3/42* (2013.01); *G01N 21/255* (2013.01); *G01J 2003/423* (2013.01)

(58) Field of Classification Search
CPC .............. G01N 21/274; G01N 21/255; G01N 21/1702; G01N 21/1704; G01N 21/17; G01N 21/25; G01N 21/27; G01N 21/31; G01N 21/39; G01N 2021/39; G01N 21/59; G01N 21/61; G01N 33/0009; G01N 33/0027; G01J 3/42; G01J 2003/423; H01S 3/06791; H01S 3/06754; H01S 3/0675
USPC ............. 250/227.11, 227.14, 227.18, 227.19; 73/24.2; 372/6, 20, 32, 29.011, 29.01, 372/29.02, 29.021; 356/477, 478, 480, 436, 356/437, 438, 439
See application file for complete search history.

(56) References Cited

U.S. PATENT DOCUMENTS 6,518,562 B1 * 2/2003 Cooper et al. ............. 250/222.2
7,145,165 B2 * 12/2006 Cox et al. ..................... 250/573
(Continued)

FOREIGN PATENT DOCUMENTS

CN 1793849 A 6/2006
CN 101532951 A 9/2009
(Continued)

OTHER PUBLICATIONS

Patent Search & Consulting Center of State Intellectual Property Office, "Search Report", Dec. 18, 2013.

*Primary Examiner* — John Lee
(74) *Attorney, Agent, or Firm* — Tim Tingkang Xia, Esq.; Morris, Manning & Martin, LLP

(57) ABSTRACT

A gas detection system with an inner ring cavity fiber laser using saturated absorption optical fiber is provided. The system comprising a ring fiber laser consisted of a pump source, a wavelength division multiplexer, a first active optical fiber, a first coupler, a fiber Bragg grating and a second coupler connected successively; an optical isolator coupled between said first active optical fiber and said first coupler; a second active grating connected between said fiber Bragg grating and said first coupler; a detection gas chamber connected between said first coupler and said second coupler; a first photoelectric detector for detecting the laser intensity outputted from said ring fiber laser to generate a first light intensity signal; a second photoelectric detector for receiving the intensity measuring beam passing through the detection gas chamber to generate a second light intensity signal; and a feedback control unit.

10 Claims, 3 Drawing Sheets

(51) Int. Cl.
*G01N 21/61* (2006.01)
*G01N 33/00* (2006.01)
*G01N 21/25* (2006.01)

(56) References Cited

U.S. PATENT DOCUMENTS

| | | | |
|---|---|---|---|
| 7,620,077 B2* | 11/2009 | Henderson | 372/6 |
| 8,144,323 B2* | 3/2012 | Majewski et al. | 356/326 |
| 8,165,178 B2* | 4/2012 | Henderson | 372/6 |
| 8,269,972 B2* | 9/2012 | Cole et al. | 356/437 |
| 8,288,727 B2* | 10/2012 | Cormier et al. | 250/339.01 |
| 8,327,686 B2* | 12/2012 | Kachanov et al. | 73/24.02 |
| 8,379,206 B2* | 2/2013 | Kachanov et al. | 356/436 |
| 8,437,000 B2* | 5/2013 | Cole et al. | 356/437 |
| 8,804,787 B1* | 8/2014 | Coleman et al. | 372/99 |
| 2002/0044575 A1 | 4/2002 | May | 372/20 |
| 2003/0030001 A1* | 2/2003 | Cooper et al. | 250/338.5 |
| 2003/0038237 A1* | 2/2003 | Webber | 250/339.12 |
| 2005/0103988 A1* | 5/2005 | Wang | 250/227.14 |
| 2006/0183241 A1* | 8/2006 | Lehmann et al. | 436/164 |
| 2007/0035810 A1* | 2/2007 | Henderson | 359/330 |
| 2007/0153839 A1* | 7/2007 | Varming et al. | 372/6 |
| 2007/0154130 A1 | 7/2007 | Tam et al. | |
| 2007/0229834 A1* | 10/2007 | Patel et al. | 356/432 |
| 2008/0137092 A1 | 6/2008 | Kraemer et al. | |
| 2010/0002234 A1* | 1/2010 | Cormier et al. | 356/436 |
| 2010/0085632 A1* | 4/2010 | Henderson | 359/341.3 |
| 2011/0214479 A1* | 9/2011 | Kachanov et al. | 73/24.02 |
| 2011/0216311 A1* | 9/2011 | Kachanov et al. | 356/213 |
| 2011/0273713 A1* | 11/2011 | Tuchman et al. | 356/437 |
| 2011/0317164 A1* | 12/2011 | Cole et al. | 356/437 |
| 2011/0317165 A1* | 12/2011 | Cole et al. | 356/437 |
| 2012/0170043 A1* | 7/2012 | Rao | 356/437 |
| 2013/0175450 A1* | 7/2013 | Scherer et al. | 250/353 |
| 2013/0228688 A1* | 9/2013 | Plusquellic et al. | 250/339.06 |
| 2014/0123729 A1* | 5/2014 | Kachanov et al. | 73/24.02 |
| 2014/0125993 A1* | 5/2014 | Kachanov et al. | 356/519 |
| 2014/0192347 A1* | 7/2014 | Koulikov et al. | 356/72 |

FOREIGN PATENT DOCUMENTS

| | | |
|---|---|---|
| CN | 103323394 A | 9/2013 |
| CN | 103335979 A | 10/2013 |

\* cited by examiner

GAS DETECTION SYSTEM USING INTRACAVITY FIBER LASER WITH LOOP CAVITY HAVING SATURATED ABSORPTION FIBER

CROSS-REFERENCE TO RELATED APPLICATIONS

This non-provisional application claims priority under 35 U.S.C. §119(a) on Patent Application No. 201310479313.5 filed in P.R. China on Oct. 14, 2013, the entire contents of which are hereby incorporated by reference.

TECHNICAL FIELD

The present invention relates to fiber laser, particularly relates to a gas detection system and method for the gas concentration measurement implemented by the inner ring cavity fiber laser with saturated absorption optical fiber.

BACKGROUND OF THE INVENTION

Laser plays an important role in modern spectroscopy, due to its high monochromaticity (narrow spectral line), high brightness, high directivity and other unique advantages. A new laser spectroscopy develops, with a high application value in various research fields such as modern agriculture and environmental science, biology and medical science, physics, chemistry and materials science and astrophysics, and in industrial process monitoring.

Laser when used for gas detection is important in environmental detection and analysis, as well as a variety of industrial process control, etc. The gas has its own characteristic spectral line, so certain kind of gas can be detected using the characteristics of the laser of narrow linewidth. One of common gas detection methods by laser is to adjust or set the wavelength emitted from the laser to be consistent with the characteristic absorption spectrum line of the gas to be detected, to transmit the laser through the gas chamber, and thus to determine the concentration of the gas by detecting the attenuation of the laser after transmitting through the gas cavity. This detecting method is simple in both the principle and the structure. However, generally the light source has a wide spectral linewidth, and some of the gases have very narrow absorption lines, so the optical power does not change obviously when passing through the gas chamber, which lowers and limits detecting sensitivity. Especially, it is more difficult for detecting tiny gas concentration.

The conventional differential absorption method is based on two beams in a common optical path passing through the same gas cavity to be detected. The output beam wavelength $\lambda 1$ of one beam is consistent with the characteristics absorption lines of the gas to be detected. And the output beam wavelength $\lambda 2$ of the adjacent beam is selected near the absorption lines of the gas to be detected, but not exactly the same with its absorption lines, to be used as a reference light in order to eliminate the instability of light intensity in the light path. However, this detection method does not eliminate the detection error caused by the instability of the wavelength of light $\lambda 1$, which can not be ignored in the practical detection. Therefore, in the prior art, the differential absorption method is improved. Commonly, the laser current and temperature is stabilized to realize a stable wavelength outputted from the laser $\lambda 1$. However such a regulation method is passive, do not strictly eliminate fluctuations of the laser $\lambda 1$, thus such an improvement do not obtain good effects.

Fiber laser is a new type laser developed rapidly in recent years. Fiber laser uses a fiber optic waveguide as a gain medium and an optical fiber grating as a feedback mirror to form an integrated optical fiber resonator, thus providing advantages such as compact structure, narrow laser linewidth, high beam quality, and a laser system with high reliability, good stability and maintenance-free, which makes a huge impact on the laser industry. Development of modern spectral composition detection and analysis system based on fiber laser will not only has great significance to the development of laser spectroscopy, but also make the fiber laser spectral analysis system more portable to be used expediently.

Therefore, it is a technical problem to be solved in this field as how to apply the fiber laser in the field of gas concentration detection taking various advantages of the fiber laser, such as its compact structure, narrow linewidth of the laser output. There is a need for a gas concentration detection method and system which not only taking advantages of fiber laser but also obtaining high sensitivity and high precision of gas detection.

SUMMARY OF THE INVENTION

The present invention provides a gas detection system with an inner ring cavity fiber laser using saturated absorption optical fiber, said system comprising: a ring fiber laser consisted of a pump source, a wavelength division multiplexer, a first active optical fiber, a first coupler, a fiber Bragg grating and a second coupler connected successively; an optical isolator coupled with said first active optical fiber and said first coupler, said optical isolator for preventing a reverse light from transmitting in said active fiber, wherein said first coupler for dividing the laser light isolated by the optical isolator into a detecting beam and an intensity measuring beam according a certain power ratio; a second active optical fiber connected between said fiber Bragg grating and said first coupler as a saturated absorber; a gas detecting chamber connected between said first coupler and said second coupler, which is introduced with the gas to be detected, and receives the detecting beam from said first coupler and makes it pass through the gas to be detected and then output to said second coupler; a first photoelectric detector connected to said first coupler for detecting the laser intensity output from said ring fiber laser to generate a first light intensity signal; a second photoelectric detector connected to said second coupler for receiving the intensity measuring beam passing through the gas detecting chamber to generate a second light intensity signal; a feedback control unit for receiving said first and second light intensity signals, and generating a feedback signal to adjust said pump source and said fiber Bragg grating.

Preferably, the power ratio of the detecting beam and the intensity measuring beam is 98:2.

Preferably, the feedback control method of the feedback control unit comprising the steps of: a) determining whether the output of the fiber laser is stable, if it is not stable, outputting a first feedback control signal to adjust the power output of the pump source until it is stable; b) determining whether the wavelength range of the signal mode outputted from the fiber laser covers the characteristics spectral lines of the gas to be detected, if it does not cover, outputting a second feedback control signal to adjust the reflectivity of fiber bragg grating until it covers; c) comparing said second light intensity signal and a reference signal stored in said feedback control unit to obtain the result of the concentration change of the gas to be detected.

Preferably, said step b) is achieved by comparing if the intensity value of said second light intensity signal is substantially smaller than that of the first light intensity signal to determine whether it covers.

Preferably, at said step c), if the intensity value of said second light intensity signal detected at present is greater than that of the stored reference signal, the concentration of the gas to be detected was reduced; if less, the concentration of the gas to be detected was increased.

Preferably, the gas detection system further comprises a laser control unit attached to the fiber Bragg grating, and the deformation of the laser control unit is controlled by said second feedback control signal so as to change the laser resonator cavity length.

Preferably, the laser control unit is made of PZT piezoelectric ceramic or TE temperature control unit.

Preferably, the wavelength division multiplexed device is a wavelength division multiplexed device of 1×2.

Preferably, the gas detection system further comprises a spherical lens for respectively coupling the detecting beam into the detection gas chamber and making the beam emit therefrom.

Preferably, the first and the second active fiber is selected from any of an ytterbium-doped fiber, erbium-doped fiber or erbium ytterbium co-doped fiber.

The present invention can take advantages of the unique superiority of the compact structure and narrow linewidth of the laser output of the fiber laser, and achieve a gas detection method with high sensitive and high precision by using a ring cavity fiber laser to obtain narrow linewidth light, connecting the gas detecting chamber inside the ring cavity fiber laser, and joining the saturated absorber to cause narrowing of the laser frequency band.

It should be understood that the foregoing general description and the following detailed description are merely exemplary explanation, and shall not be construed as limiting the contents as claimed by the invention.

BRIEF DESCRIPTION OF DRAWINGS

Further objects, functions, and advantages of the present invention will be explained in details by embodiments of the present invention with reference to the accompanying drawings.

DETAILED DESCRIPTION OF THE INVENTION

Figure 1:
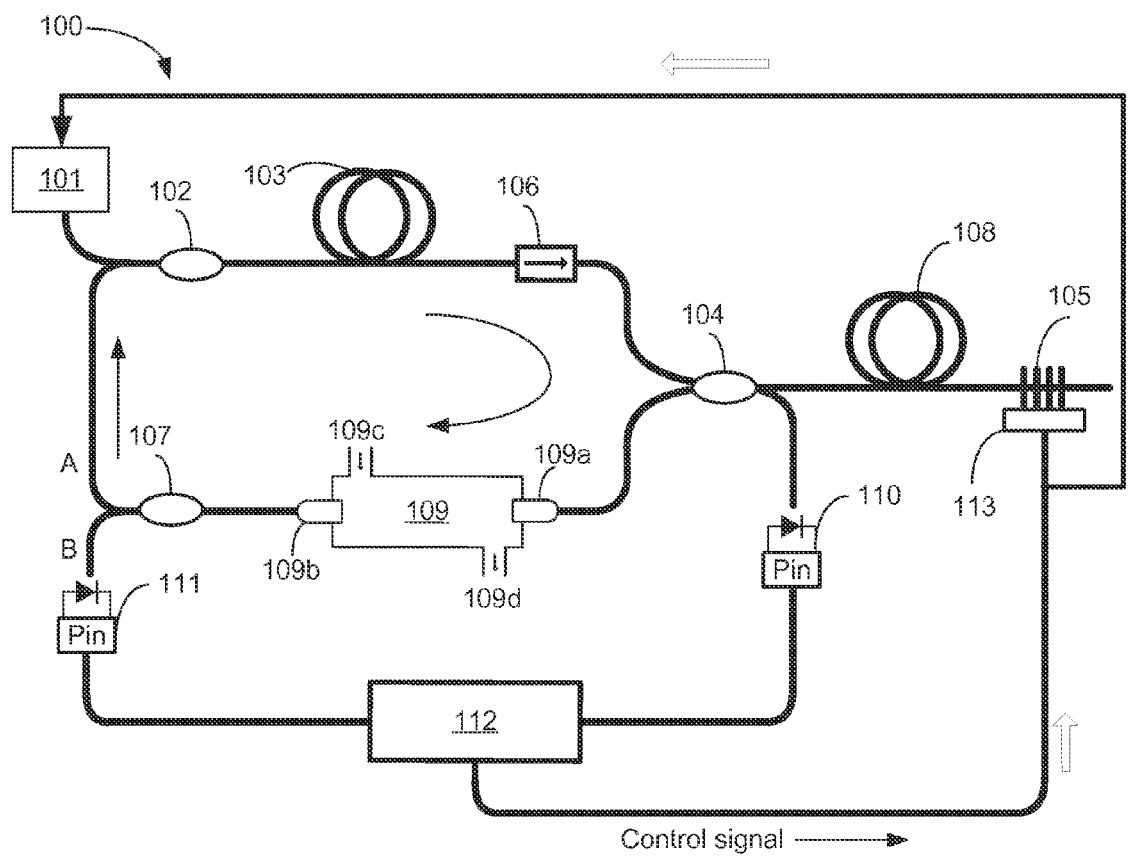
FIG. 1 schematically shows a gas detection system with an inner ring cavity fiber laser using a saturated absorption optical fiber according to the present invention.

Hereinafter, embodiments of the present invention will be explained in details with reference to drawings. In the accompanying drawings, like reference numerals designate the same or similar parts, or the same or similar procedures.

With reference to the exemplary embodiments, the purpose and function of the present invention and method to achieve these purpose and function will be explained. However, the present invention is not limited to the disclosed exemplary embodiments, and can be implemented with different forms. The description in nature is merely to help those skilled in the art to comprehensively understand the specific details of the invention.

The present invention will be described in detail with reference to the schematic figures. For the purpose of explanation, when describing the invention in details, the sectional figures representing the device structure will be partial enlarged not in general proportion, and the schematic figures are only exemplary and not intended to limit the scope claimed by the invention. Moreover, it should comprise three space dimensions of length, width and depth in the actual production.

The present invention provides a gas detection system with an inner ring cavity fiber laser using a saturated absorption optical fiber, which using a semiconductor laser as a pump source of the fiber laser, coupling the laser into a doped fiber laser by the wavelength division multiplexer (WDM), then using two couplers to constitute a ring laser structure, combining with the Fiber Bragg Grating (FBG) to realize the frequency-selecting of the output laser. Because the gas concentration will influence the loss of the laser cavity, inserting the gas chamber into the laser cavity, the gas concentration can be detected by detecting the change of the loss of the output laser after passing through the gas chamber. By inserting a active optical fiber which is not pumped as a saturated absorber (SA) between FBG and coupler, it can achieve stable single frequency laser to improve the detection accuracy.

Generally the spectral absorption detection satisfies Bill-Lambert's law as follows:

$$I(\lambda)=I_0(\lambda)\exp[-\alpha(\lambda)CL] \quad (1)$$

Wherein, the intensity of the light transmitted through the medium to be detected is denoted as I, the intensity of the light inputted into the medium to be detected is denoted as $I_0$, the molar absorption coefficient is denoted as $\alpha$, the concentration of the medium to be detected is denoted as C, and the length of the absorption path for the medium to be detected is denoted as L. Generally it is known that the incident light intensity is denoted as $I_0$, the absorption coefficient for the gas to be detected in its characteristic spectral lines is denoted as $\alpha$, the length of the gas sampling cavity for detecting the gas to be detected is denoted as L, the concentration of the gas C can detected by detecting the optical signal attenuation of the laser with the specific wavelength after it comes through the gas absorption chamber. Because a lot of gas absorption lines are narrower, it needs to compress the linewidth of the output laser and enhance the stability of the beam when using the laser as a detecting light source, Generally, the light can be interfered by various factors in the light transmission path, such as the vibration, the unstable output beam wavelength of the laser, etc. All factors will seriously interfere with the actual detection result. Considering the influence of these factors, the principle of spectral absorption detection can be revised to:

$$I(\lambda)=I_0(\lambda)K(\lambda)\exp[-\alpha(\lambda)CL+\beta(\lambda)] \quad (2)$$

Wherein, $K(\lambda)$ is the fluctuation of the light source and the light transmission path, $\beta(\lambda)$ is the detection uncertainty caused by the laser spectrum fluctuation, thus the key problem in detecting the gas concentration by the conventional absorption method is how to effectively reduce the influence on detection by $K(\lambda)$ and $\beta(\lambda)$.

FIG. 1 is a structural schematic figure which shows the gas detection system with an inner ring cavity fiber laser using a saturated absorption optical fiber according to the present invention. The gas detection system 100 according to the present invention comprises a pump source 101 which emits the pump light, and the pump light coupled into a first active optical fiber 103 to realize the amplification after passing through a wavelength division multiplexer 102, the first active optical fiber 103 connected to a optical isolator 106, then ing to the present invention should be selected to match with the pump wavelength, the laser output beam wavelength, and the parameters of the first and the second active optical fiber, the specific parameters are shown in table 1.

TABLE 1 the parameters of the short cavity fiber laser according to the present invention

| Doping element | Peak absorption | Cutoff wavelength | Cladding core diameter | output laser wavelength | WDM wavelength | FLM wavelength |
|---|---|---|---|---|---|---|
| Erbium (Er) | 30 dB/m@ 1530 nm 80 dB/m@ 1530 nm | 800-980 nm | Single mode 125 μm | 1530 nm-1560 nm | 976/1550 nm | 1550 nm |
| Ytterbium (Yb) | 280 ± 50 dB/m@ 920 nm 0.6 ± 0.2 dB/m@ 920 nm 1.8 ± 0.4 dB/m@ 920 nm | 1010 ± 70 nm | | 1060 nm-1090 nm | 915/1064 nm | 1064 nm |
| Erbium ytterbium codoping | 0.75 ± 0.15 dB/m@ 915 nm 40 ± 10 dB/m@ 1535 nm | 1440 ± 80 nm | | 1530 nm-1560 nm | 976/1550 nm | 1550 nm | connected with a first coupler 104, a fiber Bragg grating 105 and a second coupler 107 to constitute a ring fiber laser.

A second active optical fiber 108 which is not pumped is connected between the fiber Bragg grating 105 and the first coupler 104 to improve the stability of the output laser as a saturated absorber, so as to obtain single-frequency laser with narrow linewidth. The stability output of the single-frequency laser with narrow linewidth may be realized when the wavelength of the laser output is the same as the characteristics absorption lines of the gas to be detected.

A gas detecting chamber 109 filled with the gas to be detected is arranged in the resonant cavity of the ring laser, as shown in the figure, between the first coupler 104 and the second coupler 107, as a part of the ring fiber laser. When the concentration of the gas introduced into the gas detecting chamber 109 changes, a loss adjusting will occur for the laser intensity passing through the gas detecting chamber 109 to realize the change of the output laser, since the gas will absorb the light whose characteristic absorption line is the same as that of the gas.

Preferably, the wavelength division multiplexer 102 is 1×2 wavelength division multiplexer, allowing two lights of different wavelengths to transmit through a single optical fiber.

The parameters of the fiber Bragg grating 105 can be adjusted to obtain a laser output with a specified wavelength. Laser requires an output in single longitudinal mode. The narrower the output linewidth is, the better the linewidth of the output of the laser is coincident with the absorption characteristic spectral line of the gas, and the higher the accuracy for detecting gas concentration is. The first active optical fiber 103 and the second active optical fiber 108 may have shorter length (for example in cm orders of magnitude), preferably is doped with rare earth elements and has a high doping concentration (such as erbium ytterbium co-doping, peak absorption in 40+10 db/m @ 1535 nm), in order to reduce the threshold of the pump system. The fiber Bragg grating 105 has high reflectivity (the reflectance can be more than 90% for a specific wavelengths) to reduce the number of longitudinal mode of the output laser, and its center wavelength of reflection determines the center wavelength of the output beam. Laser diode pump source 101 is determined according to the absorption spectral line of active optical fiber 103 doped with rare earth elements. The parameters of the wavelength division multiplexer 102 and the fiber Bragg grating 105 accord- According to the present invention, the core diameter of the fiber is determined by the active optical fiber 103 used in the system. Cladding core diameter preferably is 125 microns, and the core diameter of the optical fiber may be 4 microns, 8 microns or 10 microns, preferably 10/125 microns. The core diameters of the FLM, WDM, LD pigtail fiber should be selected according to the selected core diameter. The pump wavelength of the Erbium-doped fiber used in this system should be 980 nm and 1480 nm, the pump wavelength of the ytterbium doped fiber should be 976 nm and 915 nm, and the pump wavelength of the erbium ytterbium doped fiber should be 976 nm. The parameters of the FLM, WDM should be determined according to the parameters of the wavelength and the core diameter. The laser wavelength outgoing finally is determined by the wavelength of reflection of the fiber Bragg grating in the gain range of the active optical fiber (such as 1530-1560 nm). The typical output beam wavelength of the ytterbium doped fiber is 1535 nm, the typical output beam wavelength of the erbium-doped fiber is 1064 nm, and the typical output beam wavelength of erbium ytterbium doped fiber is 1550 nm.

For example, in this embodiment, when an erbium-doped fiber with a core diameter of 10/125 microns is used as the gain medium, LD pigtail fiber, WDM and FLM should be selected to have the same type core diameters. The output beam wavelength of LD is 976 nm, the operating wavelength of WDM is 976/1550 nm, the operating wavelength of FLM is 1550 nm, the range of FBG is 1530 nm to 1560 nm, a laser output can obtained within this range. If in this embodiment, an ytterbium-doped fiber with a core diameter of 10/125 microns is used as the gain medium, LD fiber, WDM and FLM should be selected to have the core diameter of the same type. LD has a 915 nm single mode output, the operating wavelength of WDM is 915/1064 nm, the operating wavelength of FLM is 1064 nm, FBG is selected near 1064 nm, a laser output can be obtained in the range. The DFB fiber laser is formed by the fiber Bragg grating 105 directly writing on the active fiber 103, while the wavelength of the laser output is kept to be the same with the characteristics lines of the gas absorption are the same. The parameter selection of the second active fiber 108 is similar to the first active optical fiber 103.

The optical isolator 106 is used to prevent a reverse light from transmitting in the optical fiber, which will affect the output light of the gas detection system 100. The operating wavelength and the isolation degree of the optical isolator 106 are chosen based on the parameters of the laser emission wavelength. According to a preferable embodiment of the present invention, the operating wavelength of the optical isolator 106 is 1550 nm, and the isolation degree is 40 db.

Preferably, the first coupler 104 is 2×2 coupler, which couples the light beam transmitted through the optical isolator 106 to fiber Bragg grating 105 and couples the beam back into the gas detecting chamber 109 for detecting the gas concentration. The other output of the first coupler 104 is connected to a first photoelectric detector 110 to provide the intensity measuring beam for real-time measuring the laser intensity outputted by the ring fiber laser. According to a preferable embodiment of the present invention, the first coupler 104 has an operating wavelength of 1550 nm, a bandwidth of 40 nm, and the ratio for dividing the beam can be chosen as required. The preferred ratio for dividing the beam is such as, feedback beam:intensity measuring beam=98:2, or 95:5.

The second coupler 107 divides the light beam outputted from the gas detecting chamber 109 into two beams according to a certain power ratio, The stronger one (the light beam A as shown in the figure) is feedback to enter ring cavity of the ring fiber laser again to realize optical amplification process, and the other one (the light beam B as shown in the figure) is, as the output, connected to the second photoelectric detector 111 to receive output laser. So the concentration of the gas in the gas detecting chamber 109 can be obtained based on the change degree of the output laser. According to a preferred embodiment of the present invention, the second coupler 107 is a 1×2 coupler, and has an operating wavelength of 1550 nm, and a bandwidth of 40 nm. The ratio for dividing the beam can be selected as required. The preferred ratio for dividing the beam is such as feedback beam (A):intensity measuring beam (B)=95:5, or 90:10.

The light is coupled into the gas detecting chamber 109 by a spherical lens 109a, and then coupled out by a spherical lens 109b. The gas detecting chamber 109 is used to be filled with the gas to be detected. In the detection process, the gas inlet 109c and gas outlet 109d are opened to introduce the gas to be detected, and then closed to perform a static detection.

A first photoelectric detector 110 and a second photoelectric detector 111 are used for detecting the light intensity signal of the output light beam, wherein the second photoelectric detector 111 is used to detect the light intensity signal of the laser outputted from the fiber laser after passing through the gas detecting chamber 109, namely, the second light intensity signal, in order to detect the change of the concentration of the gas in the gas detecting chamber 109 by detecting the intensity of the laser. The first photoelectric detector 110 is used to detect the light intensity signal of the laser outputted from the fiber laser, namely, the first light intensity signal. The first light intensity signal can be used to determine whether the laser itself is operating normally, and whether the wavelength of the output beam is consistent with the absorption spectral line of the gas. The intensity of the output light beam can be detected by a power meter or spectrometer. These two light intensity signals are inputted into the feedback control unit 112 for subsequent control operations. Preferably, the photoelectric detector may be made of a photoelectric diode, and the operating wavelength range of the photoelectric detector should cover the wavelength range of the output beam of the fiber laser. According to a preferable embodiment of the invention, the operating wavelength of the photoelectric detector is 800-1700 nm, its bandwidth is 1.2 GHz, and its rise time is less than 1.0 ns.

The feedback control unit 112 is used to receive the light intensity signals outputted from the first, the second photoelectric detector 110 and 111, and then the light intensity signals are compared and calculated to output feedback control signals to the pump source 101 and the laser control unit 113 in order to implement feedback control. The feedback control unit 112 can be implemented by the single chip microcomputer, integrated circuits, application specific integrated circuits, or computer, and the control method will be described in detail below.

The laser control unit 113 preferably can be made of materials such as PZT piezoelectric ceramic or TE temperature control unit etc, which material can convert electrical signals into physical deformation, and it is used to change the cavity length of the laser resonator cavity by material deformation controlled under the feedback signal outputted from the feedback control unit 112, in order to precisely control the laser output beam wavelength. According to an embodiment of the present invention, the laser control unit 113 can be made in a shape of a sheet or plate attached on the fiber Bragg grating 105. When the feedback control unit 112 sends a control signal, physical properties of the material of the laser control unit 113 can be changed so as to change the cavity length of the laser cavity. For example, when the laser control unit 113 is made of piezoelectric ceramic, the feedback control signal makes the laser control unit 113 deform, so that the fiber bragg grating 105 attached thereto deforms, and then the length of the laser cavity changes. The wavelength of the output laser thus changes, so that the output beam wavelength drifts.

Figure 2:
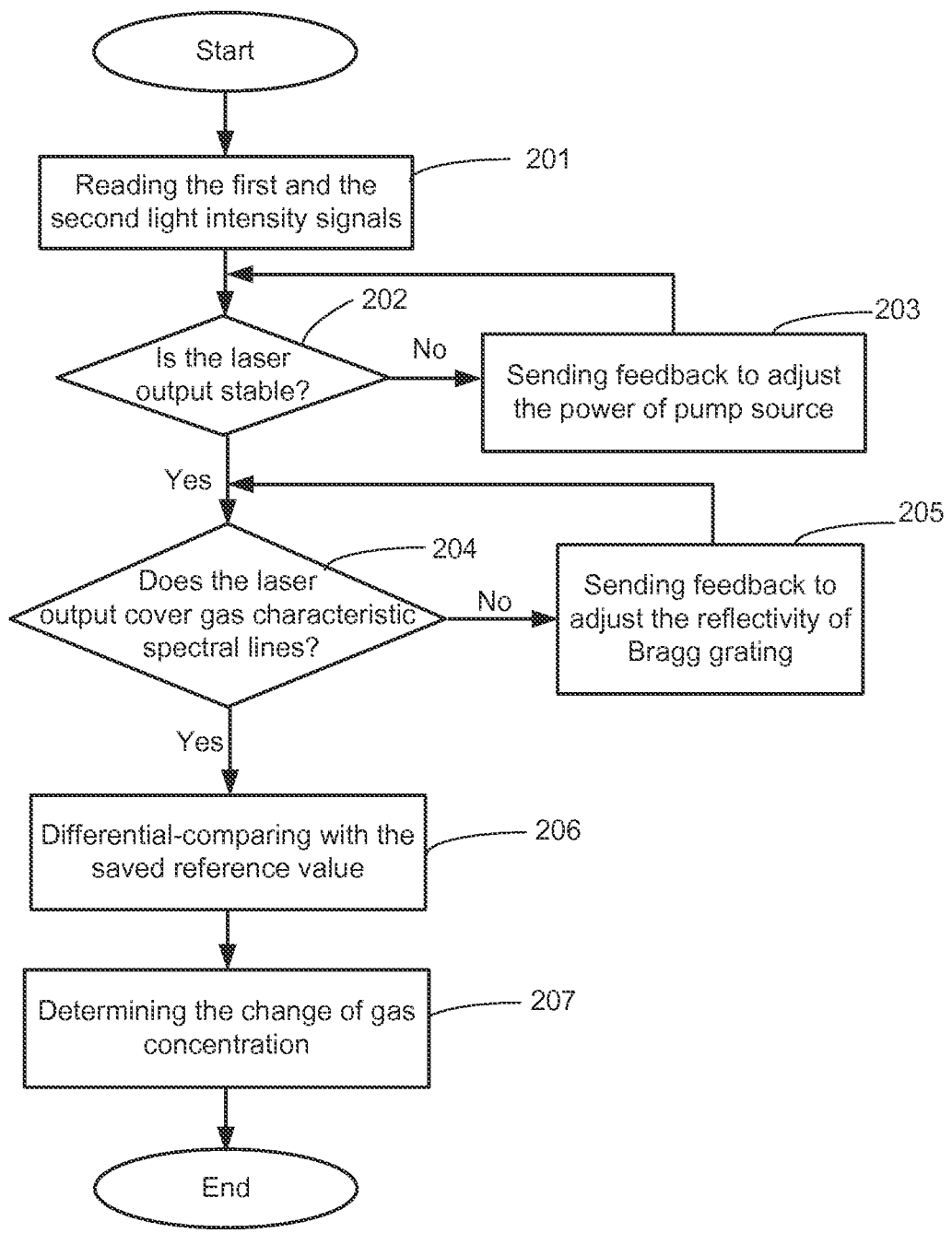
FIG. 2 schematically shows a flow chart of the feedback control method of the feedback control unit according to the present invention.

FIG. 2 shows a flow chart of the feedback control method of the feedback control unit 112 according to the present invention.

At step 201, the first light intensity signal outputted from the first photoelectric detector 110 and the second light intensity signal outputted from the second photoelectric detector 111 are read. The first light intensity signal indicates the light intensity signal outputted from the fiber laser itself, and the second light intensity signal indicates the light intensity signal of the laser outputted from the optical fiber laser after passing through the gas detecting chamber 109, as a reference signal.

In order to obtain an accurate detection result, the first and second light intensity signals are required to be stable and accurate. Therefore, firstly, at step 202, it is determined whether the output of the fiber laser is stable. Stable laser signals generally are shown as signals outputted in a shape of a step. When the system begins to operate, the pump source is usually adjusted to a level of small power output so as to protect the system. With the output power of the pump sources increases and gradually reaches the operating threshold of the laser, a stable laser output can be obtained. When at step 202 it is determined that the laser output is not stable, go to step 203, the first feedback control signal is outputted by the feedback control unit 112 to adjust the power output of the pump sources 101. For example, adjust to gradually increase the output power of pump sources. Repeat step 202 until the laser output is stable, i.e., to obtain an output signal which intensity is in a step form as required.

Figure 3:
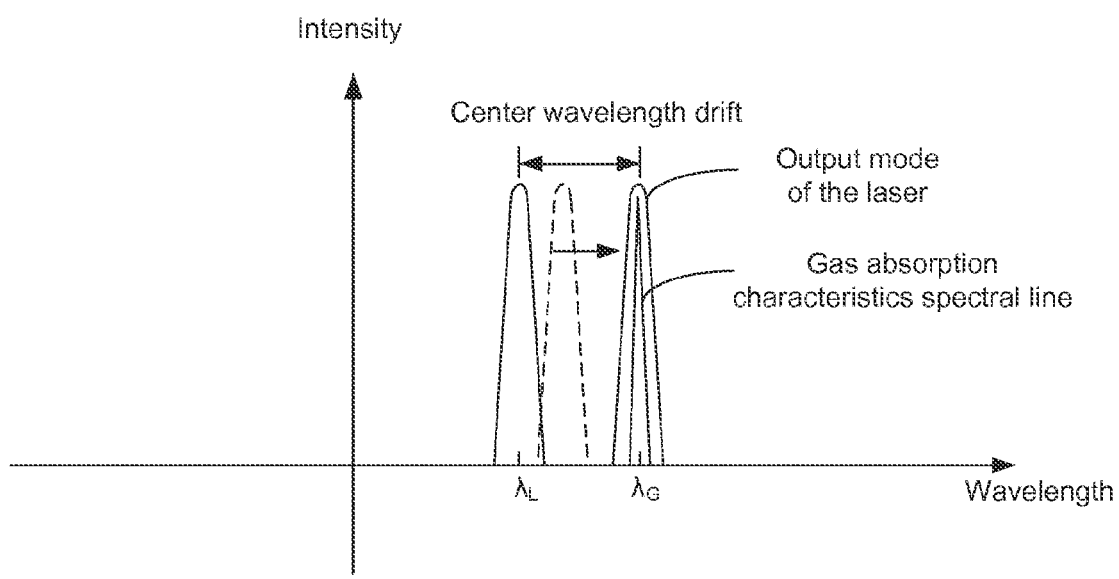
FIG. 3 schematically shows the feedback principle of feedback adjusting the drift of the laser output beam wavelength according to the present invention.

Then at step 204, it is determined whether the wavelength range of the signal model outputted from the fiber laser covers the characteristic spectral line of the gas to be detected. FIG. 3 shows the principle of feedback adjusting the drift of the output wavelength of the laser beam according to the present invention. As shown in FIG. 3, the center wavelength of the gas absorption spectral lines is denoted as $l_G$, and the center wavelength of laser output mode is denoted as $l_L$. If the concentration of the gas to be detected can be detected in a way of absorbing laser by the gas, it is needed to adjust the output of laser so that the center wavelength outputted from the laser drifts until it completely covers the center wavelength of the absorption spectral line of the gas to be detected. Ideally, when $l_G$ and $l_L$ substantially coincidence, the detection achieves the best effect. That is, the output of the laser is completely absorbed by the reference gas and the gas to be detected, and the intensity of the laser after passing through the reference chamber and the gas detecting chamber reduces significantly.

By comparing the intensity of the second light intensity signal which is absorbed by the gas in the gas detecting chamber with that of the first light intensity signal which is not absorbed by the gas, it can be determined that whether the wavelength range of the signal mode outputted from the laser covers the characteristic spectral line of the gas to be detected. If the center wavelength of the signal outputted from the fiber laser is coincident substantially with the characteristic spectral line of the gas to be detected, the laser was absorbed completely. The signal intensity of the second light intensity signal will be significantly less than the first light intensity signal without being absorbed by gas. If the wavelength does not align with the characteristic spectral line of the gas to be detected and the light is not absorbed by the gas, the signal intensity of the first light intensity signal should be substantially the same as that of the second light intensity signal. The attenuation of the second light intensity signal passing through the air chambers is negligible. The attenuation degree of the intensity of the laser absorbed by the gas compared with that of the laser not absorbed by the gas depends on the gas concentration and absorption spectral lines of the gas to be detected.

When comparing the signal intensity, it is found that the center of the wavelength of the laser output signal does not coincident with the center wavelength of the characteristics spectral line of the gas to be detected, go to step 205. The feedback control unit 112 sends a second feedback control signal to the laser control unit 113 to control the reflectivity of the Bragg grating 105, so that the laser control unit 113 will be deformed to change the laser resonator cavity length. The laser output beam wavelength will be precisely controlled to drift until it move to be substantially coincident with the center wavelength of the characteristics absorption spectral lines of the gas to be detected. For example, when the laser control unit 113 is made of piezoelectric ceramic materials in a shape of sheet or plate sheet, the laser control unit 113 deforms under the control of the feedback control signal, which makes the fiber Bragg grating 105 attached thereto deform. The laser cavity length will change, and the wavelength of the laser output will drift. Then, go to step 206.

At step 206, the second light intensity signal reflecting the gas concentration is recorded, and is compared with the value of the intensity signal of the reference light stored in the feedback control unit 112. The difference between the two intensities value indicates the changing of the concentration of the gas to be detected. For example, if the intensity value of the second light intensity signal detected at present is greater than the stored intensity value of the reference light intensity signal, less laser is absorbed when it passed through the gas detecting chamber 109, and the concentration of the gas to be detected in the gas detecting chamber 109 was reduced compared to the reference concentration. If the intensity value of the second light intensity signal detected at present is less than the stored intensity value of the reference light intensity signal, more laser was absorbed when it passed through the gas detecting chamber 109, and the concentration of the gas to be detected in the gas detecting chamber 109 was increased compared to the reference concentration. Preferably, the comparison results can be outputted to an alarm device, which may generate an alarm signal when the alarm threshold is reached.

The above reference light intensity signal can be also set as the previous detection result of the light intensity signal, thus the gas detection system according to the present invention can detect the change of the gas concentration dynamically. For example, if the intensity value of the second light intensity signal detected at present is greater than the intensity value of the light intensity signal as stored in the previous detection, less laser was absorbed when it passed through the gas detecting chamber 109, and the concentration of the gas to be detected in the gas detecting chamber 109 was reduced compared to the previous detection. If the intensity value of the second light intensity signal detected at present is less than the intensity value of the light intensity signal as stored in the previous detection, more laser was absorbed when it passed through the gas detecting chamber 109, and the concentration of the gas to be detected in the gas detecting chamber 109 was increased compared to the previous detection.

The gas detection system as above according to the present invention can be implemented to select different components parameters based on the type and the concentration of the gas to be detected. For example, the gas detection system of the present invention is applied to detect the methane content in an industrial environment. In the industrial environment, it is required that the content of methane gas is not higher than 4%, otherwise explosion will happen. When the gas detection system according to the present invention is applied, the gas detecting chamber 109 is filled with the reference gas with a methane concentration of 4%, and the components of the laser is chosen to make the wavelength range of the laser output covers the center wavelength of the absorption characteristic spectral line of methane. The system was started to detect the second light intensity signal under the current concentration of the gas, the signal intensity is recorded and kept as a signal intensity of the reference light. Then, the gas detection system is placed in the environment to be detected, the inlet of the gas detecting chamber is open so that a certain amount of gas sample to be detected is introduced into the chamber, and then the gas inlet and gas outlet of the gas detecting chamber is closed. Next, the laser of the gas detection system is enabled, so that laser light outputted from the laser passes through the gas detecting chamber. The output of the laser is detected. Next, by adjusting the power of the pump sources and the reflectivity of the fiber Bragg grating, a stable laser output is achieved to cover the absorption spectrum line of methane gas. By comparing light intensities of the reference light and the laser light passing through the gas detecting chamber, it can be determined whether methane gas concentration in this environment exceeds the threshold value of methane content, and the alarm system will be triggered immediately when it exceeds the threshold value.

The gas detection system according to the present invention has advantages of compact structure and narrow linewidth of the laser output of the fiber laser, and it can be applied in the field of gas concentration detection. According to the present invention, a gas detection method with high sensitive and high precision by feedback controlling is achieved. The method and system are not limited to apply to high sensitivity detection of gas content, but also easily apply to the detection with high sensitivity and material analysis of other materials.

Combined with the disclosed description and practice of the present invention, it is easy for those skilled in the art to contemplate and understand other embodiments of the invention. The description and embodiments are merely exemplary, and the scope and spirit of the invention will be limited by the claims.

What is claimed is:

1. A gas detection system comprising:
   a ring fiber laser comprising a pump source, a wavelength division multiplexer connected to the pump source, a first active optical fiber connected to the wavelength division multiplexer, a first coupler, a fiber Bragg grating and a second coupler;
   an optical isolator coupled between the first active optical fiber and the first coupler, for preventing reverse light from transmitting in the first active optical fiber;
   a second active optical fiber connected between the fiber Bragg grating and the first coupler as a saturated absorber;
   a detection gas chamber connected between the first coupler and the second coupler;
   a first photoelectric detector connected to the output of the first coupler;
   a second photoelectric detector connected to the second coupler;
   a feedback control unit connected to the first photoelectric detector and the second photoelectric connector,
   wherein the first coupler is configured to receive a laser light isolated by the optical isolator, divide the laser light into a first detection beam and a first intensity measuring beam according to a first power ratio, and output the first detection beam and the first intensity measuring beam;
   wherein the detection gas chamber is configured to receive gas to be detected, and receive the first detection beam outputted from the first coupler, such that he first detection beam passes through the gas to be detected to generate and output a second detection beam to the second coupler;
   wherein the second coupler is configured to divide the second detecting beam outputted from the detection gas chamber into a feedback beam and a second intensity measuring beam according to a second power ratio, and output the feedback beam and the second intensity measuring beam;
   wherein the first photoelectric detector is configured to receive the first intensity measuring beam from the first coupler, generate a first light intensity signal, and output the first light intensity signal;
   wherein the second photoelectric detector is configured to receive the second intensity measuring beam from the second coupler, generate a second light intensity signal, and output the second light intensity signal; and
   wherein the feedback control unit is configured to receive the first light intensity signal outputted from the first photoelectric detector and the second light intensity signal outputted from the second photoelectric detector, and generate at least one feedback control signal to adjust the pump source and the fiber Bragg grating.

2. The gas detection system as claimed in claim 1, wherein the first power ratio of the first detecting beam and the first intensity measuring beam is 98:2.

3. The gas detection system as claimed in claim 1, wherein the feedback control unit is configured to:
   determine whether output of the ring fiber laser is stable, if it is not stable, output a first feedback control signal to adjust power output of the pump source until it is stable;
   determine whether a wavelength range of a signal mode outputted from the ring fiber laser covers characteristics spectral lines of the gas to be detected, if it does not cover, output a second feedback control signal to adjust reflectivity of the fiber Bragg grating until it covers; and
   compare the second light intensity signal with a reference signal stored in the feedback control unit to obtain a result of concentration change of the gas to be detected.

4. The gas detection system as claimed in claim 3, wherein the feedback control unit determines whether the wavelength range of the signal mode covers the characteristic spectral lines by comparing whether a signal intensity value of the second light intensity signal is substantially smaller than that of the first light intensity signal.

5. The gas detection system as claimed in claim 3, wherein if a signal intensity value of the second light intensity signal detected at present is greater than a stored signal intensity value of the reference signal, a concentration of the gas to be detected is reduced; if less, the concentration of the gas to be detected is increased.

6. The gas detection system as claimed in claim 3, further comprising a laser control unit attached to the fiber Bragg grating, and a deformation of the laser control unit is controlled by the second feedback control signal so as to change a laser resonator cavity length.

7. The gas detection system as claimed in claim 6, wherein the laser control unit is made of PZT piezoelectric ceramic or TE temperature control unit.

8. The gas detection system as claimed in claim 1, wherein the wavelength division multiplexer is a wavelength division multiplexed device of 1×2.

9. The gas detection system as claimed in claim 1, further comprising a first spherical lens for coupling the first detecting beam into the detection gas chamber and a second spherical lens for outputting the second detecting beam from the detection gas chamber.

10. The gas detection system as claimed in claim 1, wherein the first and the second active fibers are selected from any of an ytterbium-doped fiber, erbium-doped fiber or erbium ytterbium co-doped fiber.

* * * * *